US005801252A

United States Patent [19]
Yano et al.

[11] Patent Number: 5,801,252
[45] Date of Patent: Sep. 1, 1998

[54] PROCESS FOR PRODUCTION OF CYCLIC N-VINYL CARBOXYLIC ACID AMIDE

[75] Inventors: Hitoshi Yano, Suita; Yuuji Shimasaki, Otsu, both of Japan

[73] Assignee: Nippon Shokubai Co., Ltd., Osaka, Japan

[21] Appl. No.: 820,283

[22] Filed: Mar. 18, 1997

[30] Foreign Application Priority Data

Mar. 18, 1996 [JP] Japan ................ 8-060455

[51] Int. Cl.$^6$ ............................................. C07D 207/408
[52] U.S. Cl. .............................................................. 548/554
[58] Field of Search ............................................. 548/554

[56] References Cited

U.S. PATENT DOCUMENTS

2,669,570  2/1954  Schnizer ............... 260/326

FOREIGN PATENT DOCUMENTS

| 0701998 | 3/1996 | European Pat. Off. |
| 2312422 | 9/1973 | Germany. |
| 47-040792 | 2/1971 | Japan. |
| 47-028862 | 9/1972 | Japan. |
| 48-044251 | 6/1973 | Japan. |
| 48-096584 | 12/1973 | Japan. |
| 06-256306 | 9/1994 | Japan. |

OTHER PUBLICATIONS

Tsuneki, Hideaki et. al., Development of Process for Ethylenimine Production, Nipon Kagaku Kaishi (11), 1209–1216, 1993.

Chemical Abstracts, vol. 125, No. 9, 3 Mar. 1997, Columbus, Ohio, Cui, Yingde et al: Study on preparation of poly(vinylpyrrolidone), p. 624 & Xiandai Huagong (1966), 16(6), 36–37 coden: HTKUDJ; ISSN 0253-4320, 1966.

*Primary Examiner*—Robert W. Ramsuer
*Assistant Examiner*—Dominic Keating
*Attorney, Agent, or Firm*—Sherman and Shalloway

[57] ABSTRACT

There is provided a process for producing a cyclic N-vinyl carboxylic acid amide stably in safety and low cost, using, as starting raw materials, a cyclic carboxylic acid ester and monoethanolamine both available inexpensively and easily. The process comprises subjecting a cyclic carboxylic acid ester and monoethanolamine to an intermolecular dehydration reaction (a first-step reaction) in a liquid phase to produce a cyclic N-(2-hydroxyethyl) carboxylic acid amide and then subjecting the cyclic N-(2-hydroxyethyl) carboxylic acid amide to an intramolecular dehydration reaction (a second-step reaction) in a gas phase in the presence of an oxide catalyst containing an alkali metal element and/or an alkaline earth metal element and silicon, to produce a cyclic N-vinyl carboxylic acid amide.

10 Claims, No Drawings

PROCESS FOR PRODUCTION OF CYCLIC N-VINYL CARBOXYLIC ACID AMIDE

The present invention relates to a process for producing a cyclic N-vinyl carboxylic acid amide efficiently in industry.

Cyclic N-vinyl carboxylic acid amides are useful as a raw material for various polymers. In particular, N-vinylpyrrolidone is a raw material for polyvinylpyrrolidone (polyvinylpyrrolidone finds various applications as a raw material for flocculant, agent used for paper making, agent used for oil drilling, textile auxiliary, resin additive, etc.).

Currently, N-vinyl-2-pyrrolidone, which is a representative example of cyclic N-vinyl carboxylic acid amides, is produced by a reaction represented by the following general formula (5), i.e. a Reppe process which comprises reacting 2-pyrrolidone and acetylene in the presence of a basic catalyst:

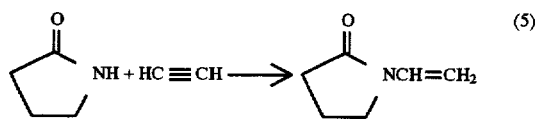

This process has the following problems although it can produce N-vinyl-2-pyrrolidone at a selectivity of about 90%.

(1) Since acetylene is handled under an applied pressure, the process involves a risk of acetylene decomposition and explosion.

(2) A higher conversion of 2-pyrrolidone results in reaction of N-vinyl-2-pyrrolidone and 2-pyrrolidone, increase in the amount of bisethylidene type by-product formed, and reduction in N-vinyl-2-pyrrolidone selectivity. Therefore, the conversion of 2-pyrrolidone must be kept at 60–70 mole % and unreacted 2-pyrrolidone must be recovered.

(3) Since the reaction is a batchwise reaction and moreover a step is necessary for production of a catalyst, i.e. an alkali metal salt of 2-pyrrolidone, the process has no satisfactory productivity.

Meanwhile, there was proposed, as a process using no acetylene, a process of reaction formula (6) which comprises subjecting N-(2-hydroxyethyl)-2-pyrrolidone to an intramolecular dehydration reaction in a gas phase in the presence of a catalyst to convert it to N-vinyl-2-pyrrolidone. In this process, N-vinyl-2-pyrrolidone can be produced without using any subsidiary material.

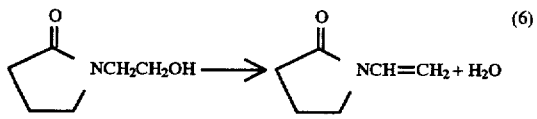

It is known that the N-(2-hydroxyethyl)-2-pyrrolidone used as a raw material in the above reaction can be produced by subjecting γ-butyrolactone and monoethanolamine to an intermolecular dehydration reaction. For example, Japanese Patent Application Laid-Open No. 48-96584 discloses a process which comprises reacting monoethanolamine and γ-butyrolactone of equimolar amount or 5–10% excessive moles relative to monoethanolamine in the presence of a small amount of water, to obtain N-(2-hydroxyethyl)-2-pyrrolidone at a high yield.

The above process of subjecting N-(2-hydroxyethyl)-2-pyrrolidone to an intramolecular dehydration reaction in a gas phase in the presence of a catalyst to convert it to N-vinyl-2-pyrrolidone, is disclosed in U.S. Pat. No. 2,669,570, Japanese Patent Application Laid-Open No. 47-18862, Japanese Patent Publication No. 47-40792, Japanese Patent Application Laid-Open No. 48-44251, Japanese Patent Application Laid-Open No. 6-256306, etc.

None of the processes disclosed in the above literatures is satisfactory for industrial application because the catalysts used are not sufficient in performance and stability of activity. Therefore, in order to carry out these processes industrially, it is requisite to develop a catalyst giving a high selectivity and simultaneously showing stable activity.

Hence, the object of the present invention is to provide a process for producing a cyclic N-vinyl carboxylic acid amide stably in safety and low cost, using, as starting materials, a cyclic carboxylic acid ester and monoethanolamine both available inexpensively and easily.

The present inventors made a study in order to achieve the above object. As a result, the present inventors found out that a cyclic N-vinyl carboxylic acid amide can be produced at a higher conversion at a higher selectivity more stably over a long period of time than in conventional processes, by subjecting a cyclic carboxylic acid ester and monoethanolamine to an intermolecular dehydration reaction (a first-step reaction) in a liquid phase to produce a cyclic N-(2-hydroxyethyl) carboxylic acid amide and then subjecting the cyclic N-(2-hydroxyethyl) carboxylic acid amide to an intramolecular dehydration reaction (a second-step reaction) in a gas phase in the presence of an oxide catalyst containing an alkali metal element and/or an alkaline earth metal element and silicon.

According to the present invention, there is provided a process for production of cyclic N-vinyl carboxylic acid amide, which comprises subjecting, to an intermolecular dehydration reaction (a first-step reaction) in a liquid phase, monoethanolamine and a cyclic carboxylic acid ester represented by the following general formula (1):

(wherein m is 0 or 1; the sum of m and n is an integer of 3–5; and one of $CH_2$s may be substituted with an oxygen atom or a sulfur atom) to form a cyclic N-(2-hydroxyethyl) carboxylic acid amide represented by the following general formula (2):

(wherein m is 0 or 1; the sum of m and n is an integer of 3–5; and one of $CH_2$ s may be substituted with an oxygen atom or a sulfur atom), and then subjecting the cyclic N-(2-hydroxyethyl)carboxylic acid amide to an intramolecular dehydration reaction (a second-step reaction) in a gas phase in the presence of an oxide catalyst containing an alkali metal element and/or an alkaline earth metal element and silicon, to form a cyclic N-vinyl carboxylic acid amide represented by the following general formula (3):

(wherein m is 0 or 1; the sum of m and n is an integer of 3–5; and one of $CH_2$ s may be substituted with an oxygen atom or a sulfur atom).

The present invention is hereinafter described in detail.
The process of the present invention is constituted by:
a step (a first-step) of subjecting a cyclic carboxylic acid ester and monoethanolamine to an intermolecular dehydration reaction represented by the following reaction formula (7):

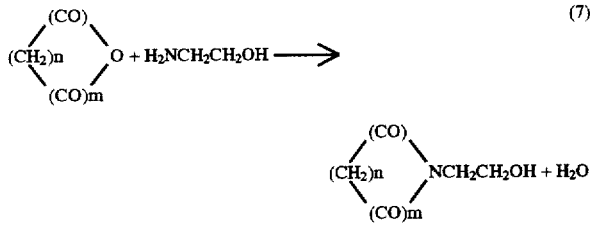

(wherein m is 0 or 1; the sum of m and n is an integer of 3–5; and one of $CH_2$ s may be substituted with an oxygen atom or a sulfur atom) in a liquid phase to produce an N-(2-hydroxyethyl) carboxylic acid amide, and a step (a second step) of subjecting the N-(2-hydroxyethyl) carboxylic acid amide to an intramolecular dehydration reaction represented by the following reaction formula (8):

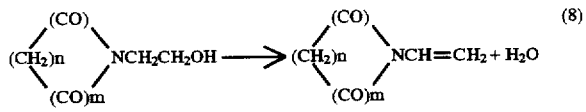

(wherein m is 0 or 1; the sum of m and n is an integer of 3–5; and one of $CH_2$ s may be substituted with an oxygen atom or a sulfur atom) in a gas phase to produce a cyclic N-vinyl carboxylic acid amide.

In the process of the present invention, the cyclic N-(2-hydroxyethyl) carboxylic acid amide used in the second-step reaction must have such a vapor pressure that the amide can keep a gaseous state under the conditions of the second-step reaction. Therefore, the cyclic carboxylic acid ester used as a starting material must be able to produce, by the intermolecular dehydration reaction (the first-step reaction) with monoethanolamine, a cyclic N-(2-hydroxyethyl) carboxylic acid amide having such a vapor pressure that the amide can keep a gaseous state under the conditions of the second-step reaction.

Examples of such a cyclic carboxylic acid ester are succinic anhydride, γ-butyrolactone, δ-valerolactone, ε-caprolactone and dioxanone. The ester is not restricted to these.

The intermolecular dehydration reaction (the first-step reaction) between cyclic carboxylic acid ester and monoethanolamine is conducted in a liquid phase. The reaction consists of (1) a ring-opening and addition reaction in which the cyclic carboxylic acid ester causes ring opening and monoethanolamine adds thereto and (2) an intramolecular dehydration reaction of the resulting adduct. It is known that when the intramolecular dehydration reaction (2) is conducted in the presence of water, the amount of tar-like by-product formed is reduced and an intended N-(2-hydroxyethyl) carboxylic acid amide can be obtained efficiently.

The intramolecular dehydration reaction (the second-step reaction) of the cyclic N-(2-hydroxyethyl) carboxylic acid amide is conducted in a gas phase. In this reaction, an oxide containing an alkali metal element and/or an alkaline earth metal element and silicon acts as an excellent catalyst. With this oxide catalyst, the cyclic N-(2-hydroxyethyl) carboxylic acid amide can be converted into a cyclic N-vinyl carboxylic acid amide continuously in one step without using any subsidiary material; therefore, a cyclic N-vinyl carboxylic acid amide can be produced simply and safely without generating any waste derived from the subsidiary material.

The catalyst used in the present process shows no substantial reduction in activity when used continuously in a long-term reaction. Even when the catalyst is deteriorated owing to the coking, etc., the catalyst can restore the activity by passing air through the catalyst to burn the coke.

The oxide catalyst containing an alkali metal element and/or an alkaline earth metal element and silicon, used in the second-step reaction of the present process is preferably an oxide represented by the following general formula:

(wherein M is at least one element selected from the group consisting of alkali metal elements and alkaline earth metal elements; Si is silicon; X is at least one element selected from the group consisting of B, Al and P; O is oxygen; and a, b, c and d are the atom numbers of M, Si, X and O, respectively, with provisos that when a=1, b is 1–500 and c is 0–1 and d is a value determined by the values of a, b and c and the bonding states of the individual constituent elements).

In the catalyst of the general formula (3), the proportion of silicon to M (which is at least one element selected from the group consisting of alkali metal elements and alkaline earth metal elements) is generally 1–500, preferably 5–200 in terms of atomic ratio, although it varies depending upon the kind of M (which is at least one element selected from the group consisting of alkali metal elements and alkaline earth metal elements).

The proportion of X as optional component (which is at least one element selected from the group consisting of B, Al and P) to M is generally appropriate to be 0–1 in terms of atomic ratio, although it varies depending upon the kind of M and the proportion of Si.

The catalyst of the present invention has no particular restriction as to the production process and can be produced by any known process. With respect to the alkali metal element and/or the alkaline earth metal element, which is an essential element of the present catalyst, the raw material thereof can be an oxide, a hydroxide, a halide, a salt (e.g. carbonate, nitrate, carboxylate, phosphate or sulfate), a metal or the like. With respect to silicon, which is another essential component, the raw material thereof can be silicon oxide, silicic acid, a silicic acid salt (e.g. alkali metal silicate or alkaline earth metal silicate), a silicon-containing molecular sieve (e.g. aluminosilicate or silicoaluminophosphate), an organic silicic acid ester or the like. With respect to X, which is an optional component, the raw material thereof can be an oxide, a hydroxide, a halide, a salt (e.g. carbonate, nitrate, carboxylate, phosphate or sulfate), a metal or the like.

The calcination temperature employed in production of the catalyst is 300°–1,000° C., preferably 400°–800° C. although it varies depending upon the kinds of the raw materials for catalyst.

The reactor used for the first-step reaction can be any of a batchwise type, a semi-batchwise type and a flow type.

The first-step reaction consists of (1) a ring-opening and addition reaction in which the cyclic carboxylic acid ester causes ring opening and monoethanolamine adds thereto and (2) an intramolecular dehydration reaction of the resulting adduct. The ring-opening and addition reaction (1) generally takes place quantitatively at room temperature or higher. Meanwhile, the intramolecular dehydration reaction (2) of the adduct proceeds at 150°–400° C. The temperature of the reaction (2), however, varies depending upon the kind of the cyclic carboxylic acid ester used and, when the cyclic carboxylic acid ester is γ-butyrolactone or succinic anhydride, the temperature is 180°–300° C. As described previously, when the intramolecular dehydration reaction (2) is conducted in the presence of water, the amount of tar-like by-product formed is reduced and an intended N-(2-hydroxyethyl) carboxylic acid amide can be obtained at a high yield.

The reactor used for the second-step reaction can be any of a fixed bed flow type and a fluidized bed type.

The second-step reaction is conducted at such a reaction temperature and reaction pressure that the raw material [N-(2-hydroxyethyl) carboxylic acid amide] can keep a gaseous state. The reaction pressure can be generally normal pressure or a reduced pressure, but may be an applied pressure. The reaction temperature is generally 300°–500° C., preferably 350°–450° C. although it varies depending upon other reaction conditions. When the reaction temperature is lower than 300° C., the conversion of raw material [N-(2-hydroxyethyl) carboxylic acid amide] is reduced substantially; when the temperature is higher than 500° C., the selectivity of intended product (N-vinyl carboxylic acid amide) is reduced substantially. The raw material [N-(2-hydroxyethyl) carboxylic acid amide] is fed into a catalyst layer by diluting it with a substance (e.g. nitrogen, helium, argon or hydrocarbon) inert to the reaction or employing a reduced pressure so that the raw material has a partial pressure of 5–600 mmHg. The gas hourly space velocity (GHSV) of the raw material is generally 1–1,000 $h^{-1}$, preferably 10–500 $h^{-1}$ although it varies depending upon the kind of the raw material [N-(2-hydroxyethyl) carboxylic acid amide] and other reaction conditions.

The present invention is described in more detail below by way of Examples. The present invention is in no way restricted by these Examples.

In the Examples, conversion, selectivity and yield have the following definitions.

[First-step reaction]

Conversion (mole %)=[(moles of monoethanolamine consumed)/(moles of monoethanolamine fed)]×100

Selectivity (mole %)=[(moles of N-(2-hydroxyethyl) carboxylic acid amide formed)/(moles of monoethanolamine consumed)]×100

Yield (mole %)=[(moles of N-(2-hydroxyethyl) carboxylic acid amide formed)/(moles of monoethanolamine fed)]×100

[Second-step reaction]

Conversion (mole %)=[(moles of N-(2-hydroxyethyl) carboxylic acid amide consumed)/(moles of N-(2-hydroxyethyl) carboxylic acid amide fed)]×100

Selectivity (mole %)=[(moles of N-vinyl carboxylic acid amide formed)/(moles of N-(2-hydroxyethyl) carboxylic acid amide consumed)]×100

Yield (mole %)=[(moles of N-vinyl carboxylic acid amide formed)/(moles of N-(2-hydroxyethyl) carboxylic acid amide fed)]×100

[Through-yield from first-step reaction to second-step reaction]

The through-yield from first-step reaction to second-step reaction, based on monoethanolamine is defined as follows, because the unreacted raw material in the second-step reaction can be recovered and reused.

Through-yield (mole %)=(yield in first-step reaction)×(selectivity in second-step reaction)×100

EXAMPLE 1

[First-step reaction]

356 g of monoethanolamine and 100 g of water were fed into a 1-liter autoclave purged with nitrogen, at room temperature. Thereto was added 518 g of γ-butyrolactone with stirring. After the completion of the addition, the autoclave inside was pressurized to 30 atm. with nitrogen and then heated to 250° C. to give rise to a reaction for 2 hours. Immediately thereafter, the autoclave inside was cooled and the reaction mixture was analyzed by gas chromatography. As a result, the conversion of monoethanolamine was 100 mole %, and the selectively and yield of N-(2-hydroxyethyl)-2-pyrrolidone were both 94 mole %.

[Second-step reaction]

The reaction mixture obtained in the first-step reaction was subjected to distillation and purification to obtain N-(2-hydroxyethyl)-2-pyrrolidone, and the product was used as a raw material.

<Catalyst production>

7.76 g of cesium carbonate was dissolved in 250 g of water. Thereto was added 30 g of silicon oxide with stirring at 90° C. The mixture was heated and concentrated. The concentrate was dried in air at 120° C. for 20 hours. The resulting solid was crushed into 9–16 mesh and calcined in air at 500° C. for 2 hours to obtain a catalyst having a composition of $Cs_1Si_{10}$ in terms of atomic ratio when oxygen was excluded.

<Reaction>

30 ml of the catalyst was filled in a stainless steel-made reaction tube having an inner diameter of 15 mm. The reaction tube was dipped in a molten salt bath of 360° C. Into the reaction tube was fed a raw material gas consisting of N-(2-hydroxyethyl)-2-pyrrolidone and nitrogen, at a pyrrolidone space velocity of 200 $h^{-1}$, and a reaction was conducted at normal pressure. The raw material gas was prepared by diluting N-(2-hydroxyethyl)-2-pyrrolidone with nitrogen so that the partial pressure of N-(2-hydroxyethyl)-2-pyrrolidone became 76 mmHg. The reactor outlet gas after 1 hour from the start of the reaction was collected with methanol and analyzed by gas chromatography. As a result, the conversion of N-(2-hydroxyethyl)-2-pyrrolidone and the selectivity and yield of N-vinyl-2-pyrrolidone were 94 mole %, 93 mole % and 87 mole %, respectively.

The through-yield (from the first-step reaction to the second-step reaction) of N-vinyl-2-pyrrolidone based on monoethanolamine was 87 mole %.

EXAMPLE 2

[First-step reaction]

A reaction and analysis were conducted in the same manner as in the first-step reaction of Example 1 except that 518 g of γ-butyrolactone was replaced by 583 g of succinic anhydride and the reaction temperature was changed to 200° C. The conversion of monoethanolamine was 100 mole %, and the selectivity and yield of N-(2-hydroxyethyl) succinimide were both 92 mole %.

[Second-step reaction]

A reaction and analysis were conducted in the same manner as in the second-step reaction of Example 1 except that (1) there was used, as the raw material, N-(2-hydroxyethyl)succinimide obtained by subjecting the reaction mixture obtained in the first-step reaction of Example 2, to distillation and purification, (2) the reaction temperature was changed to 400° C., (3) the partial pressure was changed to 38 mmHg, and (4) the space velocity was changed to 100 $h^{-1}$. After 1 hour from the start of feeding, the conversion of N-(2-hydroxyethyl)succinimide and the selectivity and yield of N-vinylsuccinimide were 89 mole %, 84 mole % and 75 mole %, respectively.

The through-yield (from the first-step reaction to the second-step reaction) of N-vinylsuccinimide based on monoethanolamine was 77 mole %.

EXAMPLES 3–6

[First-step reaction]

Conducted in the same manner as in the first-step reaction of Example 1.

[Second-step reaction]

<Catalyst production>

Catalysts shown in Table 1 (the compositions are expressed each in atomic ratio when oxygen was excluded) were produced in the same manner as in the catalyst production of Example 1 except that 3.45 g of lithium nitrate was changed to 4.25 g of sodium nitrate (Example 3), 5.06 g of potassium nitrate (Example 4), 7.38 g of rubidium nitrate (Example 5) and 9.75 g of cesium nitrate (Example 6).

<Reaction>

Reactions were conducted in the same manner as in the second-step reaction of Example 1 except that the above catalysts were used and the reaction temperature used in Example 1 was changed. The results of analysis after 1 hour from the start of feeding are shown in Table 1.

TABLE 1

| No. of Example | Catalyst | Reaction temp. (°C.) | Conversion (mole %) | Selectivity (mole %) | Yield (mole %) | Through-yield (mole %) |
| --- | --- | --- | --- | --- | --- | --- |
| 3 | $Na_1Si_{10}$ | 310 | 57 | 99 | 56 | 93 |
| 4 | $K_1Si_{10}$ | 370 | 86 | 95 | 82 | 89 |
| 5 | $Rb_1Si_{10}$ | 370 | 89 | 94 | 84 | 88 |
| 6 | $Cs_1Si_{10}$ | 350 | 81 | 96 | 78 | 90 |

Comparative Example 1

A reaction and analysis were conducted in the same manner as in the second-step reaction of Example 1 except that the catalyst was changed to active alumina (a product obtained by conducting calcination at 500° C. for 2 hours). After 1 hour from the start of feeding, the conversion of N-(2-hydroxyethyl)-2-pyrrolidone and the selectivity and yield of N-vinyl-2-pyrrolidone were 94 mole %, 34 mole % and 32 mole %, respectively. The through-yield from the first-step reaction to the second-step reaction was 32 mole %.

Comparative Example 2

A reaction and analysis were conducted in the same manner as in the second-step reaction of Example 1 except that the catalyst was changed to zirconium oxide (a product obtained by conducting calcination at 900° C. for 2 hours). After 1 hour from the start of feeding, the conversion of N-(2-hydroxyethyl)-2-pyrrolidone and the selectivity and yield of N-vinyl-2-pyrrolidone were 85 mole %, 71 mole % and 60 mole %, respectively. The through-yield from the first-step reaction to the second-step reaction was 67 mole %.

EXAMPLE 7

[First-step reaction]

Conducted in the same manner as in the first-step reaction of Example 1.

[Second-step reaction]

<Catalyst production>

30 g of a spherical silica gel (5–10 mesh) was dipped in a solution of 0.41 g of cesium carbonate dissolved in 40 g of water, for 2 hours. The resulting material was concentrated on a hot water bath. The concentrate was dried in air at 120° C. for 20 hours and then calcined in air at 800° C. for 2 hours to obtain a catalyst having a composition of $Cs_1Si_{200}$ in terms of atomic ratio when oxygen was excluded.

<Reaction>

A reaction and analysis were conducted in the same manner as in the second-step reaction of Example 1 except that the catalyst was changed to the above catalyst. After 1 hour from the start of feeding, the conversion of N-(2-hydroxyethyl)-2-pyrrolidone and the selectivity and yield of N-vinyl-2-pyrrolidone were 91 mole %, 91 mole % and 83 mole %, respectively. The through-yield from the first-step reaction to the second-step reaction was 86 mole %.

EXAMPLE 8

[First-step reaction]

Conducted in the same manner as in the first-step reaction of Example 1.

[Second-step reaction]

<Catalyst production>

30 g of a spherical silica gel (5–10 mesh) was dipped in a solution of 4.36 g of barium nitrate dissolved in 100 g of water, for 2 hours. The resulting material was concentrated on a hot water bath. The concentrate was dried in air at 120° C. for 20 hours and then calcined in air at 500° C. for 2 hours to obtain a catalyst having a composition of $Ba_1Si_{30}$ in terms of atomic ratio when oxygen was excluded.

<Reaction>

A reaction and analysis were conducted in the same manner as in the second-step reaction of Example 1 except that the catalyst was changed to the above catalyst and the reaction temperature was changed to 380° C. After 1 hour from the start of feeding, the conversion of N-(2-hydroxyethyl)-2-pyrrolidone and the selectivity and yield of N-vinyl-2-pyrrolidone were 73 mole %, 91 mole % and 66 mole %, respectively. The through-yield from the first-step reaction to the second-step reaction was 86 mole %.

EXAMPLE 9

[First-step reaction]

Conducted in the same manner as in the first-step reaction of Example 1.

[Second-step reaction]

<Catalyst production>

30.0 g of silicon oxide was added to a solution of 19.5 g of cesium nitrate and 4.9 g of boric acid dissolved in 100 g of water. The mixture was concentrated with stirring on a hot water bath. The concentrate was dried in air at 120° C. for 20 hours, crushed into 9–16 mesh, and calcined in air at 500° C. for 2 hours to obtain a catalyst having a composition of $Cs_1Si_5B_{0.8}$ in terms of atomic ratio when oxygen was excluded.

<Reaction>

A reaction and analysis were conducted in the same manner as in the second-step reaction of Example 1 except that the catalyst was changed to the above catalyst. After 1 hour from the start of feeding, the conversion of N-(2-hydroxyethyl)-2-pyrrolidone and the selectivity and yield of N-vinyl-2-pyrrolidone were 85 mole %, 97 mole % and 82 mole %, respectively. The through-yield from the first-step reaction to the second-step reaction was 91 mole %.

EXAMPLE 10

[First-step reaction]

Conducted in the same manner as in the first-step reaction of Example 1.

[Second-step reaction]

<Catalyst production>

1.2 g of aluminum phosphate and 30 g of silicon oxide were added to a solution of 19.5 g of cesium nitrate and 9.2 g of diammonium phosphate dissolved in 100 g of water. The mixture was concentrated with stirring on a hot water bath. The concentrate was dried in air at 120° C. for 20 hours, crushed into 9–16 mesh, and calcined in air at 600° C. for 2 hours to obtain a catalyst having a composition of $Cs_1Si_5Al_{0.1}P_{0.8}$ in terms of atomic ratio when oxygen was excluded.

<Reaction>

A reaction and analysis were conducted in the same manner as in the second-step reaction of Example 1 except that the catalyst was changed to the above catalyst. After 1 hour from the start of feeding, the conversion of N-(2-hydroxyethyl)-2-pyrrolidone and the selectivity and yield of N-vinyl-2-pyrrolidone were 54 mole %, 98 mole % and 53 mole %, respectively. The through-yield from the first-step reaction to the second-step reaction was 92 mole %.

EXAMPLE 11

[First-step reaction]

Conducted in the same manner as in the first-step reaction of Example 1.

[Second-step reaction]

<Catalyst production>

30 g of silicon oxide was added to a solution of 4.25 g of sodium nitrate and 1.32 g of diammonium phosphate dissolved in 100 g of water. The mixture was concentrated with stirring on a hot water bath. The concentrate was dried in air at 120° C. for 20 hours, crushed into 9–16 mesh, and calcined in air at 600° C. for 2 hours to obtain a catalyst having a composition of $Na_1Si_{10}P_{0.2}$ in terms of atomic ratio when oxygen was excluded.

<Reaction>

5 ml of the catalyst was filled in a stainless steel-made reaction tube. The reaction tube was dipped in a molten salt bath of 380° C. The inside of the reaction tube was made vacuum by the use of a vacuum pump, and N-(2-hydroxyethyl)-2-pyrrolidone was fed thereinto under the conditions of reactor outlet pressure=76 mmHg and space velocity=400 $h^{-1}$. After 1 hour from the start of feeding, the conversion of N-(2-hydroxyethyl)-2-pyrrolidone and the selectivity, yield and through-yield of N-vinyl-2-pyrrolidone were 80 mole %, 99 mole %, 79 mole % and 93 mole %, respectively. Those after 100 hours from the start of feeding were 79 mole %, 99 mole %, 78 mole % and 93 mole %, respectively.

EXAMPLE 12

[First-step reaction]

Conducted in the same manner as in the first-step reaction of Example 1.

[Second-step reaction]

<Catalyst production>

8.15 g of cesium carbonate was dissolved in 100 g of water. Thereto was added 30 g of silicon oxide. The mixture was concentrated with stirring on a hot water bath. The concentrate was dried in air at 120° C. for 20 hours. The resulting material was crushed into 9–16 mesh and calcined in air at 500° C. for 2 hours to obtain a catalyst having a composition of $Cs_1Si_{10}$ in terms of atomic ratio when oxygen was excluded.

<Reaction>

30 ml of the catalyst was filled in a stainless steel-made reaction tube having an inner diameter of 15 mm. The reaction tube was dipped in a molten salt bath of 360° C. Into the reaction tube was fed a raw material gas consisting of N-(2-hydroxyethyl)-2-pyrrolidone and nitrogen, at a pyrrolidone space velocity of 200 $h^{-1}$, and a reaction was conducted at normal pressure. The raw material gas was prepared by diluting N-(2-hydroxyethyl)-2-pyrrolidone with nitrogen so that the partial pressure of N-(2-hydroxyethyl)-2-pyrrolidone became 76 mmHg. The reactor outlet gas after 1 hour from the start of the reaction was collected with methanol and analyzed by gas chromatography. As a result, the conversion of N-(2-hydroxyethyl)-2-pyrrolidone and the selectivity and yield of N-vinyl-2-pyrrolidone were 94 mole %, 93 mole % and 87 mole %, respectively. The through-yield from the first-step reaction to the second-step reaction was 87 mole %.

EXAMPLE 13

[First-step reaction]

A reaction and analysis were conducted in the same manner as in the first-step reaction of Example 1 except that 518 g of γ-butyrolactone was replaced by 583 g of succinic anhydride and the reaction temperature was changed to 200° C. The conversion of monoethanolamine was 100 mole %, and the selectivity and yield of N-(2-hydroxyethyl) succinimide were both 92 mole %.

[Second-step reaction]

A reaction and analysis were conducted in the same manner as in the second-step reaction of Example 1 except that (1) there was used, as the raw material, N-(2-hydroxyethyl)succinimide obtained by subjecting the reaction mixture obtained in the first-step reaction of Example 2, to distillation and purification, (2) the reaction temperature was changed to 400° C., (3) the partial pressure was changed to 38 mmHg, and (4) the space velocity was changed to 100 $h^{-1}$. After 1 hour from the start of feeding, the conversion of N-(2hydroxyethyl)succinimide and the selectivity and yield of N-vinylsuccinimide were 89 mole %, 84 mole % and 75 mole %, respectively. The through-yield from the first-step reaction to the second-step reaction was 77 mole %.

As is demonstrated by the above Examples, the present process enables continuous production of a cyclic N-vinyl carboxylic acid amide from a cyclic carboxylic acid ester and monoethanolamine via an N-(2-hydroxyethyl) carboxylic acid amide, without using any subsidiary material. Since no waste derived from subsidiary material is generated, the present process is very simple and safe in industrial application.

What is claimed is:

1. A process for production of cyclic N-vinyl carboxylic acid amide, which comprises subjecting, to an intermolecular dehydration reaction in a first-step reaction in a liquid phase, monoethanolamine and a cyclic carboxylic acid ester represented by the following general formula (1):

wherein m is 0 or 1; the sum of m and n is an integer of 3–5; and one of the $CH_2$ s may be substituted with an oxygen atom or a sulfur atom to form a cyclic N-(2-hydroxyethyl)

carboxylic acid amide represented by the following general formula (2):

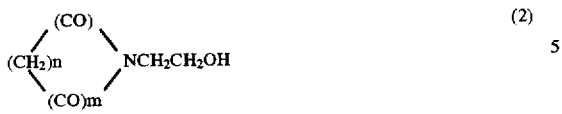  (2)

wherein m is 0 or 1; the sum of m and n is an integer of 3–5; and one of the CH$_2$ s may be replaced by an oxygen atom or a sulfur atom, and then subjecting the cyclic N-(2-hydroxyethyl)carboxylic acid amide to an intramolecular dehydration reaction in a second-step reaction in a gas phase in the presence of an oxide catalyst containing an alkali metal element and/or an alkaline earth metal element and silicon, to form a cyclic N-vinyl carboxylic acid amide represented by the following general formula (3):

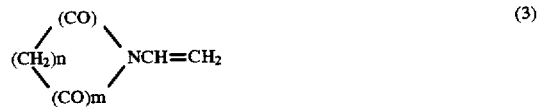  (3)

wherein m is 0 or 1; the sum of m and n is an integer of 3–5; and one of the CH$_2$ s may be replaced by an oxygen atom or a sulfur atom, and wherein the second step reaction catalyst is an oxide represented by the following general formula (4):

  (4)

wherein M is at least one element selected from the group consisting of alkali metal elements and alkaline earth metal elements; Si is silicon; X is at least one element selected from the group consisting essentially of boron, has been aluminum; O is oxygen; and a, b, c and d are the atom numbers of M, Si, X and O, respectively, with provisos that when a=1, b is 1–500 and c is 0–1, and d is a value determined by the values of a, b, and c and the bonding states of the individual constituent elements.

2. A process according to claim 1, wherein the cyclic carboxylic acid ester is γ-butyrolactone, the cyclic N-(2-hydroxyethyl)carboxylic acid amine is N-(2-hydroxyethyl)-2-pyrrolidone, and the cyclic N-vinyl carboxylic acid amide is N-vinyl-2-pyrrolidone.

3. A process according to claim 1, wherein the cyclic carboxylic acid ester is succinic anhydride, the cyclic N-(2-hydroxyethyl)carboxylic acid amide is N-(2-hydroxyethyl)-succinimide, and the cyclic N-vinyl carboxylic acid amide is N-vinylsuccinimide.

4. The process of claim 1, wherein the alkali metal is a member selected from the group consisting of sodium and potassium and the alkaline earth metal is a member selected from the group consisting of cesium, rubidium and barium.

5. The process of claim 1, wherein m is 0 and n is an integer of 4–5.

6. The process of claim 1, wherein the cyclic carboxylic acid is a member selected from the group consisting of valerolactone and ε-caprolactone.

7. The process of claim 1, wherein in the second step reaction catalyst

  (4)

M is a member selected from the group consisting of sodium, potassium, cesium, rubidium and barium, b is 5 to 200 and c is 0.

8. A process for production of cyclic N-vinyl carboxylic acid amide, which comprises subjecting, to an intermolecular dehydration reaction in a first-step reaction in a liquid phase, monoethanolamine and a cyclic carboxylic acid ester represented by the following general formula (1):

  (1)

wherein m is 1; the sum of m and n is an integer of 3–5; and one of CH$_2$ s may be substituted with an oxygen atom or a sulfur atom to form a cyclic N-(2-hydroxyethyl) carboxylic acid amide represented by the following general formula (2):

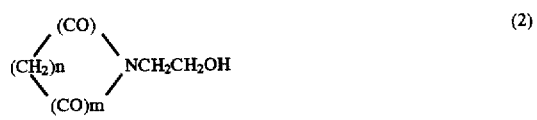  (2)

wherein m is 1; the sum of m and n is an integer of 3–5; and one of the CH$_2$ s may be replaced by an oxygen atom or a sulfur atom, and then subjecting the cyclic N-(2-hydroxyethyl)carboxylic acid amide to an intramolecular dehydration reaction in a second-step reaction in a gas phase in the presence of an oxide catalyst containing an alkali metal element and/or an alkaline earth metal element and silicon, to form a cyclic N-vinyl carboxylic acid amide represented by the following general formula (3):

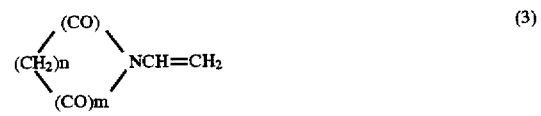  (3)

wherein m is 1; the sum of m and n is an integer of 3–5; and one of the CH$_2$ s may be replaced by an oxygen atom or a sulfur atom, and wherein the second step reaction catalyst is an oxide represented by the following general formula (4):

  (4)

wherein M is at least one element selected from the group consisting of alkali metal elements and alkaline earth metal elements; Si is silicon; X is at least one element selected from the group consisting essentially of boron, has been aluminum; O is oxygen; and a, b, c and d are the atom numbers of M, Si, X and O, respectively, with provisos that when a=1, b is 1–500 and c is 0–1, and d is a value determined by the values of a, b, and c and the bonding states of the individual constituent elements.

9. The process of claim 8, wherein the alkali metal is a member selected from the group consisting of sodium and potassium and the alkaline earth metal is a member selected from the group consisting of cesium, rubidium and barium.

10. The process of claim 8, wherein in the second step reaction catalyst

  (4)

M is a member selected from the group consisting of sodium, potassium, cesium, rubidium and barium, b is 5 to 200 and c is 0.

* * * * *

UNITED STATES PATENT AND TRADEMARK OFFICE
CERTIFICATE OF CORRECTION

PATENT NO. : 5,801,252
DATED : September 1, 1998
INVENTOR(S) : Hitoshi YANO AND Yuuji SHIMASAKI It is certified that error appears in the above-indentified patent and that said Letters Patent is hereby corrected as shown below:

Col. 7, Table 1, Example 3 reaction temperature, delete "310" and insert --370--

Signed and Sealed this

Second Day of February, 1999

Attest:

Attesting Officer

*Acting Commissioner of Patents and Trademarks*